United States Patent
Kim et al.

(10) Patent No.: US 11,787,747 B2
(45) Date of Patent: *Oct. 17, 2023

(54) POLYCHROMATIC ZIRCONIA BODIES AND METHODS OF MAKING THE SAME

(71) Applicant: James R. Glidewell Dental Ceramics, Inc., Newport Beach, CA (US)

(72) Inventors: Dongkyu Kim, Irvine, CA (US); Akash, Irvine, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 106 days.

This patent is subject to a terminal disclaimer.

(21) Appl. No.: 17/227,546

(22) Filed: Apr. 12, 2021

(65) Prior Publication Data
US 2021/0230077 A1 Jul. 29, 2021

Related U.S. Application Data

(63) Continuation of application No. 16/260,640, filed on Jan. 29, 2019, now Pat. No. 10,974,997.

(Continued)

(51) Int. Cl.
*C04B 41/00* (2006.01)
*C04B 41/45* (2006.01)
(Continued)

(52) U.S. Cl.
CPC ............ *C04B 41/009* (2013.01); *A61K 6/818* (2020.01); *C04B 35/486* (2013.01); *C04B 41/457* (2013.01); *C04B 41/4535* (2013.01); *C04B 41/89* (2013.01); *C04B 2111/82* (2013.01); *C04B 2235/3224* (2013.01);
(Continued)

(58) Field of Classification Search
CPC ... A61B 18/00; A61C 13/004; C04B 41/5048; C04B 41/009
See application file for complete search history.

(56) References Cited

U.S. PATENT DOCUMENTS 7,845,924 B2  12/2010  Cadario et al.
7,981,531 B2   7/2011  Rheinberger et al.
(Continued)

FOREIGN PATENT DOCUMENTS

WO  2004031103 A1   4/2004
WO  2004103303 A1  12/2004
WO  2014206439 A1  12/2014

OTHER PUBLICATIONS

Guanwei Liu et al., Fabrication of coloured zirconia ceramics by infiltrating water debound injection moulded green body. Research Gate, Advances in Applied Ceramics, Jan. 2011, in 6 pages.

*Primary Examiner* — Dah-Wei D. Yuan
*Assistant Examiner* — Andrew J Bowman
(74) *Attorney, Agent, or Firm* — Charles Fowler

(57) ABSTRACT

A ceramic body is provided that is suitable for use in dental applications to provide a natural aesthetic appearance. A colorized ceramic body is formed that has at least one color region and a color gradient region. A ceramic body is formed having at least two color regions and a color gradient that forms a transition region between two color regions. A method for making the colorized ceramic body includes unidirectional infiltration of a coloring composition into the ceramic body.

19 Claims, 5 Drawing Sheets

Related U.S. Application Data

(60) Provisional application No. 62/635,644, filed on Feb. 27, 2018, provisional application No. 62/623,102, filed on Jan. 29, 2018.

(51) Int. Cl.
*C04B 35/486* (2006.01)
*C04B 41/89* (2006.01)
*A61K 6/818* (2020.01)
*C04B 111/82* (2006.01)

(52) U.S. Cl.
CPC ............ *C04B 2235/3241* (2013.01); *C04B 2235/3275* (2013.01); *C04B 2235/44* (2013.01); *C04B 2235/606* (2013.01); *C04B 2235/616* (2013.01); *C04B 2235/6567* (2013.01); *C04B 2235/77* (2013.01); *C04B 2235/9661* (2013.01)

(56) References Cited

U.S. PATENT DOCUMENTS

| | | | |
|---|---|---|---|
| 8,025,992 B2 | 9/2011 | Engels et al. | |
| 8,298,329 B2 | 10/2012 | Knapp et al. | |
| 8,721,336 B2 | 5/2014 | Rheinberger et al. | |
| 8,936,848 B2 | 1/2015 | Jung et al. | |
| 8,962,146 B2 | 2/2015 | Giordano | |
| 9,039,947 B2 | 5/2015 | Jahns et al. | |
| 9,095,403 B2 | 8/2015 | Carden et al. | |
| 9,212,065 B2 | 12/2015 | Yamada et al. | |
| 9,365,459 B2 | 6/2016 | Carden et al. | |
| 9,434,651 B2 | 9/2016 | Carden | |
| D769,449 S | 10/2016 | Leeson et al. | |
| 9,512,317 B2 | 12/2016 | Carden et al. | |
| 9,649,179 B2 | 5/2017 | Jung et al. | |
| 9,872,746 B2 | 1/2018 | Hauptmann et al. | |
| 9,949,808 B2 | 4/2018 | Wolz | |
| 10,034,728 B2 | 7/2018 | Jung et al. | |
| 2005/0175552 A1 | 8/2005 | Hoic et al. | |
| 2008/0241551 A1 | 10/2008 | Zhang et al. | |
| 2013/0316305 A1 | 11/2013 | Carden et al. | |
| 2015/0173869 A1 | 6/2015 | Jung et al. | |
| 2015/0223917 A1 | 8/2015 | Herrmann et al. | |
| 2016/0120765 A1 | 5/2016 | Dang et al. | |
| 2016/0228223 A1 | 8/2016 | Jung | |
| 2017/0157645 A1 | 6/2017 | Wolz | |
| 2017/0189143 A1* | 7/2017 | Wolz | A61K 6/802 |
| 2017/0245970 A1 | 8/2017 | Jung et al. | |
| 2017/0304031 A1 | 10/2017 | Jung et al. | |
| 2017/0304032 A1 | 10/2017 | Jung et al. | |

\* cited by examiner

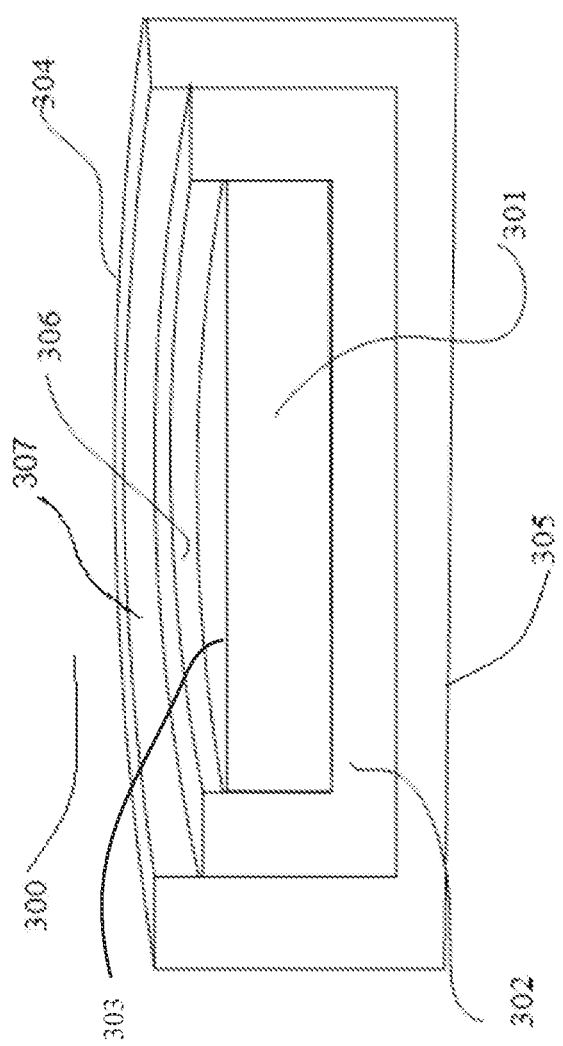

POLYCHROMATIC ZIRCONIA BODIES AND METHODS OF MAKING THE SAME

This application is a continuation of, and claims the benefit of and priority to, U.S. patent application Ser. No. 16/260,640, filed Jan. 29, 2019, which claims the benefit of and priority to U.S. Provisional Patent Application No. 62/635,644, filed Feb. 27, 2018 and U.S. Provisional Patent Application No. 62/623,102, filed Jan. 29, 2018, the entireties of each of which applications are incorporated herein by reference.

BACKGROUND

Colorization of porous, millable ceramic blocks is known. Through conventional processes including dipping, spraying, and painting, coloring liquids may infiltrate pores of a pre-sintered ceramic body enhancing the appearance of ceramic material. Colored ceramic blocks have applications as dental restorations, such as crowns, bridges, partial and full dentures. However, conventional colorization methods that yield single colored ceramic blocks may be unsuitable for making dental restorations that match the appearance of natural dentition in which color is smoothly variable over the surface.

To achieve the aesthetics of natural dentition in ceramic restorations, attempts have been made to create a polychromatic appearance. For example, in some methods pigment is applied by hand-painting; however, the results of the labor-intensive method depend largely on the skill of the dental technician. In other conventional methods, batches of ceramic powder with multiple colors are pressed as individual layers to form multi-layered blocks, which can be milled into polychromatic restorations. However, making powder batches with multiple colors and providing storage may be costly.

A further method attempts to target the distribution of color pigments in a porous ceramic by a convection flow. The flow direction and velocity are regulated by environmental parameter gradients, such as air humidity gradient, pressure gradient, and/or temperature gradient. Controlled directional movement of color pigment is attempted by changing the direction of one or more parameters of the convective flow.

SUMMARY

A polychromatic ceramic body suitable for use in dental restoration applications having a natural appearance is provided. A method for making the polychromatic ceramic body, and a device for coloring the ceramic body, are also provided. In one embodiment, the ceramic body comprises a discrete color region, having a uniform color throughout the region, and a gradient color region adjacent the discrete color region. In another embodiment, a polychromatic ceramic body comprises two or more color regions arranged from the top surface of the ceramic body to bottom surface (y-axis direction). In a further embodiment, a transition region comprising a smooth color gradient is located between two color regions. Each color region may comprise substantially uniform color across the diameter or width of a ceramic body, and the ceramic body may be any shape, including but not limited to, cylinder, disc, or polyhedron, such as a cube or prism.

Color regions of a minable ceramic block may be tailored to provide a first color or shade at a top region of the ceramic block and a second color or shade that is lighter than the first shade at a bottom region. A computer design of a dental restoration, such as a restoration tooth or denture design, may be nested so that a cervical and/or body region is milled from a darker shaded top portion, and an incisal region is milled from the lighter bottom region. The lighter, bottom region may, optionally, have greater translucency than the top region, creating a natural incisal appearance in a finished dental restoration. Advantageously, a color transition region eliminates sharp boundaries between two color regions that may occur in traditional processes. The resulting dental restorations may comprise a smooth color or shade gradient between the body region and incisal region of a restoration tooth.

A method for making the polychromatic ceramic body comprises the unidirectional infiltration of a liquid coloring composition into and through a portion of the porous ceramic body (in the y-axis direction). Prior to infiltration, side surfaces of the ceramic body may be rendered impermeable to coloring compositions during the infiltration process, thereby restricting the ingress and egress of liquid coloring compositions through side surfaces, contributing to the unidirectional movement of liquid coloring compositions from a top surface to a bottom surface. In one embodiment, between top and bottom surfaces, curved side surface of a ceramic disc or cylinder, or sides and side edges of a polyhedron, are covered with a casing material that is resistant to penetration by the liquid coloring composition during infiltration. Bottom surfaces and edges between bottom and side surfaces, may also be covered to resist the ingress or egress of liquid coloring composition into or out of the porous ceramic body from any surface other than the top surface.

A smooth color gradient may be formed by infiltrating a liquid coloring composition into a first portion of a porous ceramic body, fixing (e.g. by heating) a portion of the infiltrated liquid coloring composition at one end of the ceramic body to prevent further infiltration of a portion of the infiltrated liquid coloring composition, and thereby forming a color region. The remaining (non-fixed) portion of the infiltrated liquid coloring composition may continue to diffuse through the thickness of a second portion of the porous ceramic body forming a color gradient region adjacent the color region. A color gradient has a greater concentration of coloring agent adjacent the region infiltrated by liquid coloring composition and lesser concentration of coloring agent as the distance from the region increases. In another embodiment, the smooth color gradient may be accomplished by introducing a diluting liquid within a first region of the ceramic body prior to infiltrating a liquid coloring composition. A smooth color gradient forms as a portion of the liquid coloring composition that has been infiltrated into a second region, mixes with a portion of the infiltrated diluting liquid, and the diluted coloring composition gradually infiltrates or diffuses further into the ceramic body.

In a further embodiment, a porous ceramic body covered by a casing material on side and bottom surfaces is infiltrated by a liquid coloring composition that occupies substantially, the entire pore volume of the ceramic body. After sintering, a monochromatic body is formed having a uniform color throughout the mass of the sintered ceramic body.

In a further embodiment, a method has been made for improving machinability of a polychromatic ceramic body. In one embodiment, a bisque or partially sintered porous ceramic body that is infiltrated with a liquid coloring composition is heated to a temperature below the sintering temperature of the ceramic for a period of time, to facilitate milling of the colorized ceramic body.

BRIEF DESCRIPTION OF THE FIGURES

FIG. 3 is a cross-sectional illustration of an embodiment of an infiltration set-up.

DETAILED DESCRIPTION

A method is disclosed for providing color to a ceramic body through an infiltration technique. A ceramic body is provided that has one or more color regions, and optionally, a color gradient region. In another embodiment, a ceramic body is provided having at least two color regions and a color gradient region that forms a transition region between two color regions. A method for making a polychromatic ceramic body, and a device for coloring a ceramic body, are disclosed. Single shaded and polychromatic ceramic blocks are suitable for use in making dental restorations, such as ceramic dental restoration teeth and bridges, having a natural appearance.

Figure 1:
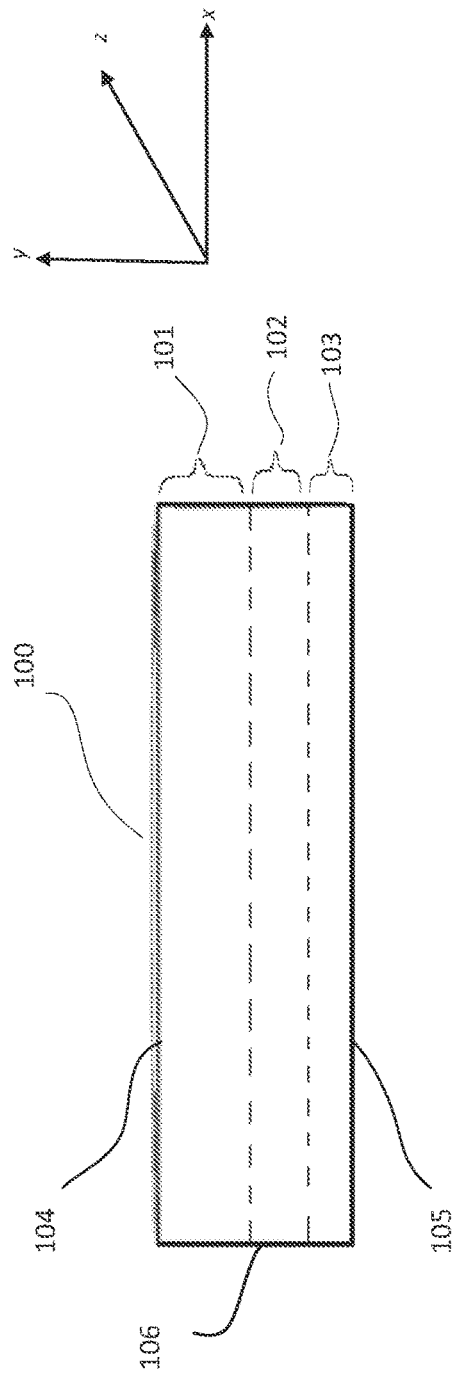
FIG. 1 is a perspective view of an embodiment of a sectioned polychromatic body.

In an exemplary embodiment, illustrated in FIG. 1, a polychromatic ceramic body (100) comprises two or more color regions (101, 103) and a color transition region (102) providing a smooth color gradient there between. In this embodiment, individual color regions (101, 103) and color transition region (102) are arranged from a top surface (104) of the ceramic body to a bottom surface (105) along an axis (referred to herein as y-axis direction, as illustrated in FIG. 1). A color transition region (102) provides a gradual transition (illustrated in FIG. 1 by broken lines) between the color of a first region (101) and the color of a second region (103). As illustrated in FIG. 1, a color region (101, 102, 103) extends between outer side surfaces (106) across the width or diameter (x and z axis direction) of the ceramic body, for a selected height (in the y-axis direction).

The polychromatic ceramic body, illustrated in FIG. 1 as a disc-shaped body, may be any shape suitable for use in making dental restorations. In one embodiment, a dental restoration crown milled from the polychromatic ceramic body, comprises a cervical area (e.g., adjacent the gingiva when installed) and/or a body portion that is milled from a darker color region (101), and an incisal region (e.g. adjacent an incisal edge) that is milled from a lighter color region (103), of the ceramic body. The crown comprises a smooth color gradient between cervical/body region and incisal region shades, providing a natural appearance.

A method for making the polychromatic ceramic body comprises unidirectionally, infiltrating a liquid coloring composition into a portion of the porous ceramic body (in the y-axis direction). Prior to infiltration, the outer side surface (106) is covered with a casing that extends from the top edge, adjacent the top surface (104), to the bottom edge, adjacent the bottom surface (105). Casing material may prevent the flow of the liquid coloring composition in the x-axis and z-axis directions by inhibiting ingress and/or egress through the side surface(s), and optionally, bottom surface, of the porous ceramic body during the infiltration step.

Where the ceramic body is a ceramic disc or cylinder, the permeation resistant casing material may be in direct contact with the porous ceramic surfaces covering the entire curved outer side surface from the top to the bottom of the ceramic body. Where the ceramic body is a polyhedron, the sides and joining edges may be covered with the casing material. Bottom surfaces (105), and edge(s) between bottom and side surfaces, may also be covered by contact with a casing that inhibits the ingress or egress of liquid into and/or out of the porous ceramic body from any surface other than the top surface (104).

A casing suitable for use herein hinders movement of infiltrating liquids into or out of surfaces of the porous ceramic body to which the casing material is applied, such as liquid coloring composition and/or diluting liquid. Casing materials may comprise waterproof, water resistant and/or chemically resistant materials. Suitable materials maintain contact with the porous surfaces during infiltration processes, and resist penetration by infiltrating liquids (e.g., liquid coloring composition and/or diluting liquid) throughout the infiltration process. For example, casing materials may withstand penetration or chemical degradation by acidic liquid coloring compositions during the infiltration process, preventing the introduction of liquid coloring composition into covered portions of the porous ceramic body. Casing materials may be applied by conventional processes for covering a surface, including, but not limited to, coating, wrapping, or adhering the material onto ceramic body surfaces. Flexible or stretchable materials may be shaped to form a permeation resistant body into which the porous ceramic body is inserted. Casing materials suitable for use herein, include, but are not limited to, plastic or rubber materials, and polymeric materials such as polyurethane or fluorinated polymers.

Figure 2:
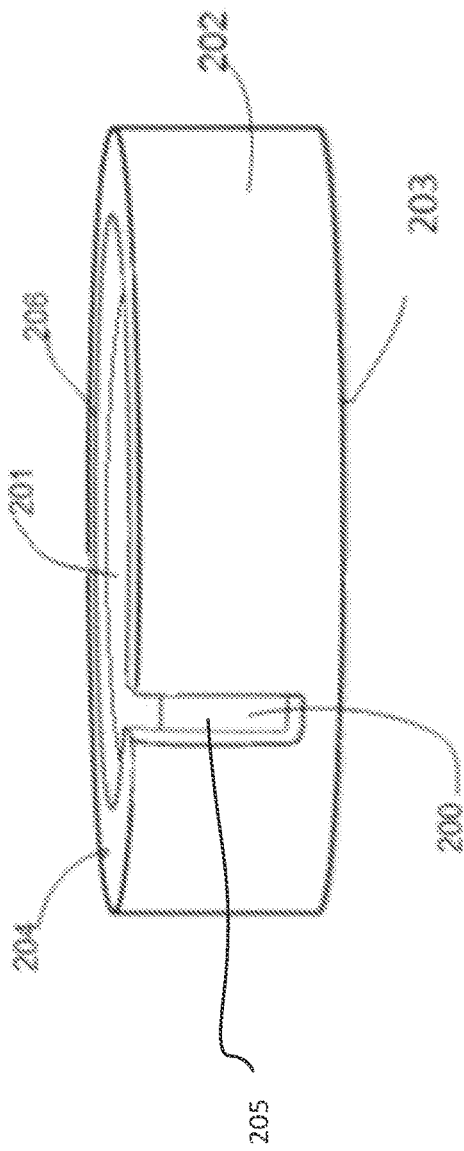
FIG. 2 is a perspective view of one embodiment of a ceramic body in a casing with a cut-out of a portion of the casing surrounding the ceramic body.

As illustrated by the embodiment in FIG. 2, a ceramic body (200) is contained in a casing in which only the top surface (201) is not covered. A cutaway of the casing is provided for illustrative purposes, demonstrating a side surface (205) of the ceramic body (200) and an inner side wall of the casing material in tight-fitting relationship, preventing liquid components from moving out of, or in through, the ceramic body outer surfaces to which it contacts. In one embodiment, the casing (202) may comprise a flexible or resilient material that bends or stretches to accommodate the ceramic body, surrounding, contacting and conforming to the entire side surface of ceramic body (200) from the top edge to the bottom; a bottom portion (203) of the casing conforms to the bottom surface and a bottom edge to prevent movement of a liquid coloring solution into or out of the ceramic body through the bottom surface. The casing side wall (204) may extend above the top surface (201) of the ceramic body to form a reservoir (206) that holds a volume of liquid coloring composition directly on the top surface (201) of the ceramic body during infiltration.

FIG. 3 illustrates a cross-sectioned perspective view of one embodiment of an infiltration set-up (300). A porous ceramic body (301) is contained within a permeation-resistant casing (302) having a side wall and bottom that tightly conforms to the side and bottom surfaces of the porous body (301). In this embodiment, both the casing and the ceramic body are placed within a container (304) that has an opening (307) for introducing a volume of liquid coloring composition into the infiltration set-up, directly onto the top surface of the porous ceramic body (301), opposition a bottom (305) of the container. The container is comprised of a material suitable for supporting the casing during the infiltration process, including, but not limited to, plastic, glass and ceramic. The container may be inert, resistant to penetration and/or resistant to degradation, by the liquid coloring composition, a diluting liquid, or both.

In the embodiment illustrated in FIG. 3, the side wall of the container (304) and casing (302) extend beyond the top edge of the ceramic body and form the reservoir (306) adjacent the infiltration surface (e.g. top surface) of the porous ceramic body. The liquid coloring composition is held in the reservoir in contact with the top surface of the porous, ceramic body during the infiltration process. The liquid coloring composition infiltrates into an upper region of the porous ceramic body adjacent the top surface over a period of time. In one embodiment, the infiltration depth of the liquid coloring composition is at least 1 mm from the top surface, or at least 5 mm from the top surface, or at least 10 mm from the top surface, or between 1 mm and 20 mm from the top surface, or between 5 mm and 14 mm from the top surface, of the ceramic body. In another embodiment, the infiltration depth of the liquid coloring composition is in the range of 10% to 95%, or 10% to 100%, of the height of the porous ceramic body measured in the y-axis direction from an end surface, (e.g. the top surface.) Infiltration may proceed for a sufficient time for the liquid coloring composition to uniformly infiltrate to a desired distance from the infiltration surface. Excess liquid coloring composition that has not been infiltrated may be removed from contact with the top surface (303). In one embodiment, infiltrated liquid coloring composition may continue to infiltrate or diffuse, unidirectionally, toward the bottom surface of the ceramic body to occupy a target region, until the coloring composition is fixed (e.g. by heating). The ceramic body may be heated, fixing metal-containing components of the coloring agent, and inhibiting further diffusion of the coloring agent through the ceramic body.

In one embodiment, a first portion of the liquid coloring composition is fixed in an upper region (101) (e.g. by heating) to prevent further diffusion of the fixed portion into the ceramic body. A second portion of the liquid coloring composition that has not been fixed, a non-fixed portion, may continue to diffuse or to infiltrate, unidirectionally, toward the bottom surface of the porous ceramic body. The second portion of the liquid coloring composition may then be fixed to terminate further diffusion, fixing the second portion of the coloring composition between the upper region (101) and a lower region (103), and the second portion may form a color transition region (102) between the upper region and lower region. The color transition region (102) forms a smooth color gradient lacking discernable color transition lines between the transition region and the upper and lower regions, when viewed with the unaided eye.

The dimensions of the color regions and color gradient regions may be designed to be the same or different. In one embodiment, a first color region, a second color region and a color gradient region each comprise approximately one third of the height (y-axis direction) of a sintered ceramic body, uniformly through the entire width or thickness. The dimension of the upper region may be controlled, for example, by controlling the volume of liquid coloring composition that infiltrates the upper region. The dimension of the upper region may also be controlled by the amount of liquid coloring composition that is fixed in the upper region before further diffusing to form the transition region. The location and dimension of the transition region may be selected by controlling the amount of coloring liquid that infiltrates prior to fixing the coloring liquid to form a first color region, and/or by controlling the amount of diffusion that occurs prior to a final heating step that fixes the coloring agent and terminates further diffusion.

Figure 4A:
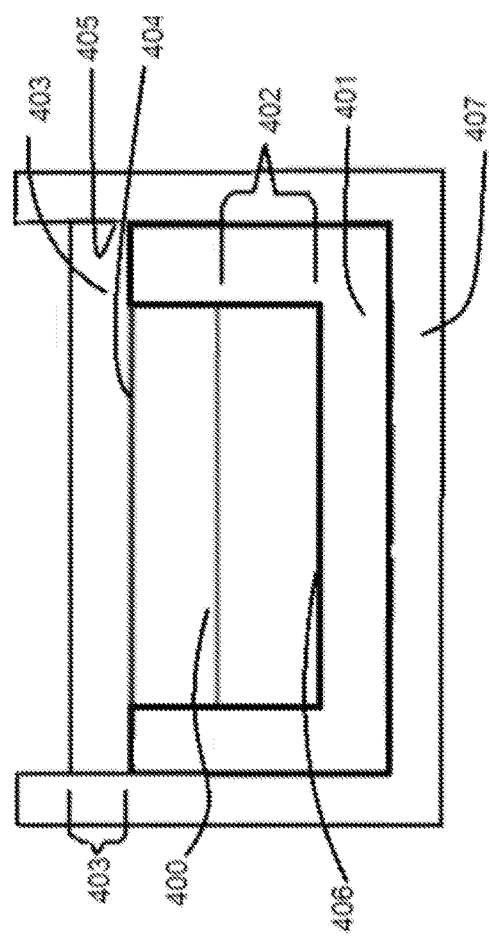
FIGS. 4a and 4b are cross-sectional illustrations of one embodiment of an infiltration process and set-up according to the invention.

Illustrated in the exemplary embodiment of FIG. 4a, the ceramic body (400) is contained within a casing (401), and placed in a container (407) to form an infiltration set-up. The ceramic body is illustrated having a first region that has been infiltrated by a diluting liquid (402) adjacent a bottom surface (406). A volume of liquid coloring composition (403) is contained within a reservoir formed by side walls (405) of the container (407) and the exposed, top surface (404) of the ceramic body. The liquid coloring composition (403) infiltrates through the top surface (404) in a downward direction into a second region of the porous body. In this embodiment, the liquid coloring composition (403) contacts the diluting liquid (402) at an interface between the liquid coloring composition and the diluting liquid. Within the porous ceramic body, a portion of the coloring agent of the liquid coloring composition diffuses into the diluting liquid forming a continuous gradient as the coloring agent concentration decreases from a lower portion of the second region that comprises the liquid coloring composition to an upper portion of the first region that comprises the diluting liquid.

Figure 4B:
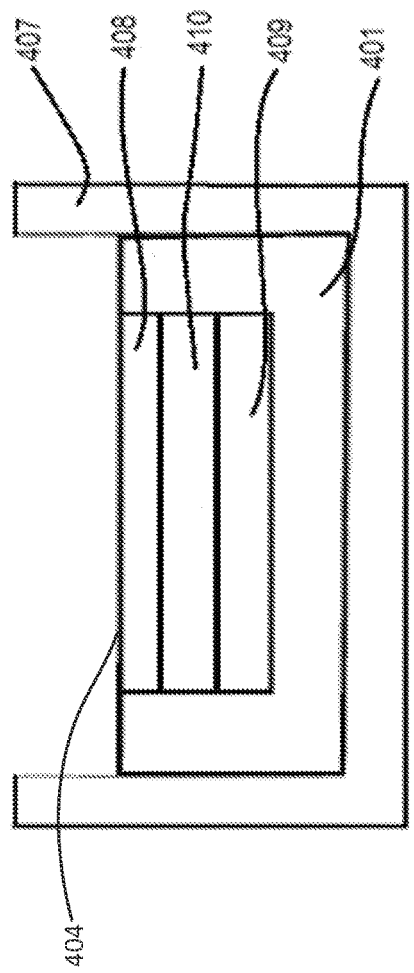

In the exemplary embodiment of FIG. 4b, after infiltration and diffusion of liquid coloring composition, three regions are formed in the porous ceramic. An upper region (408) of the porous ceramic body predominantly contains the liquid coloring composition within the pore volume, and a lower region (409) predominantly contains the diluting liquid. A transition region (410) is formed between upper and lower regions upon dilution of a portion of the liquid coloring composition. A smooth color gradient is formed as the concentration of coloring agent within the transition region gradually decreases within the transition region.

Figure 5:
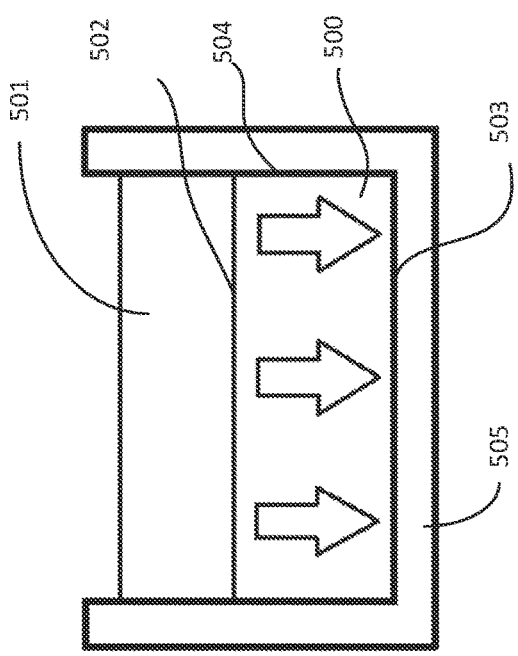
FIG. 5 is a cross-sectional illustration of an embodiment of a unidirectional infiltration process and set-up for making a monochromatic ceramic body.

In a further embodiment, illustrated in FIG. 5, a colored, ceramic body is formed having a uniform color between top and bottom surfaces throughout the mass of the ceramic body. In this embodiment, a volume of liquid coloring composition (501) is provided adjacent a top surface (502) that uniformly infiltrates the entire porous ceramic body (500) from the top surface (502) to the bottom surface (503) (as indicated by the arrows). Prior to infiltration, the porous ceramic body (500) is covered on side (504) and bottom (503) surfaces by a casing material (505) preventing the passage of liquid through the side surface and bottom surface of the ceramic body. Upon sintering, a monochromatic ceramic body is formed, having a single shade from top to bottom, with no color gradient region.

Figure 6B:
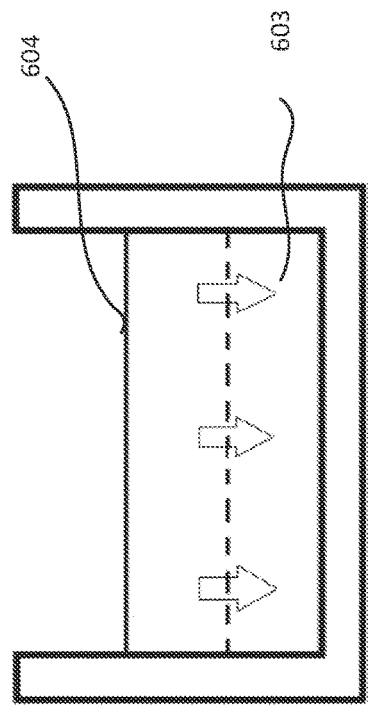
FIGS. 6a and 6b are cross-sectional illustrations of an embodiment of a unidirectional infiltration process for making a polychromatic ceramic body having a color region and a transition region.
Figure 6A:
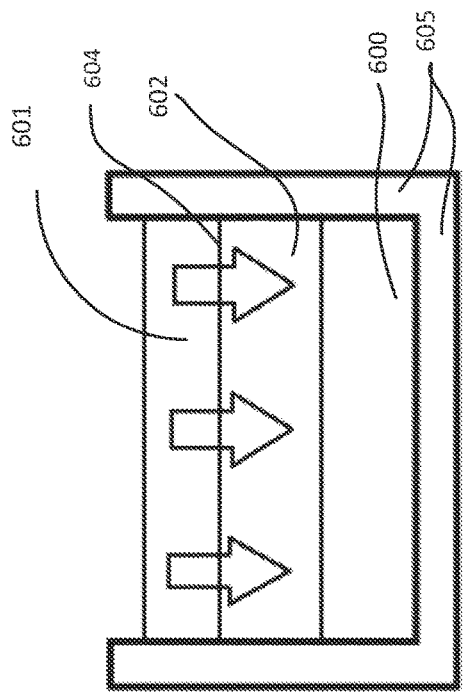

In a separate embodiment, illustrated in FIG. 6a, a ceramic body (600) is covered by a casing material (605) on side surfaces and bottom surfaces, and a volume of liquid coloring composition (601) is adjacent an exposed top surface of the porous ceramic body. The ceramic body (600) is infiltrated by the liquid coloring composition (601) which fills a top region (602) of the porous ceramic body (600).

The volume of liquid coloring composition (601) that contacts the exposed top surface (604) of the ceramic body, infiltrates unidirectionally, in a top-to-bottom direction (as indicated by the arrows). As illustrated in FIG. 6b, after infiltrating the top region (602), excess liquid coloring composition is removed from the top surface, and liquid coloring composition and/or the coloring agent component, unidirectionally infiltrates or diffuses (as indicated by the arrows) into a second region (603) forming a gradient region.

Figure 7A:
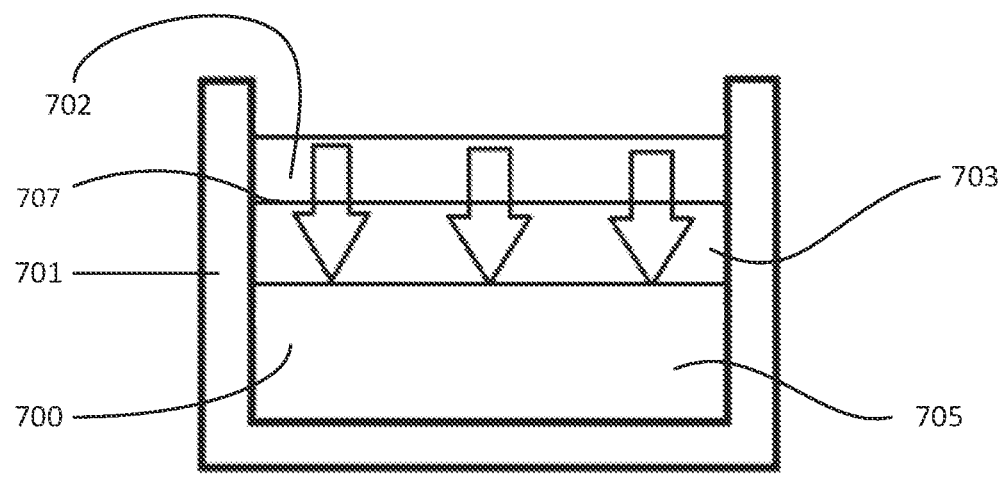
FIGS. 7a, 7b, and 7c, are cross-sectional illustrations of an embodiment of a sequential, unidirectional infiltration process for making a polychromatic ceramic body having a transition region between two color regions.
Figure 7B:
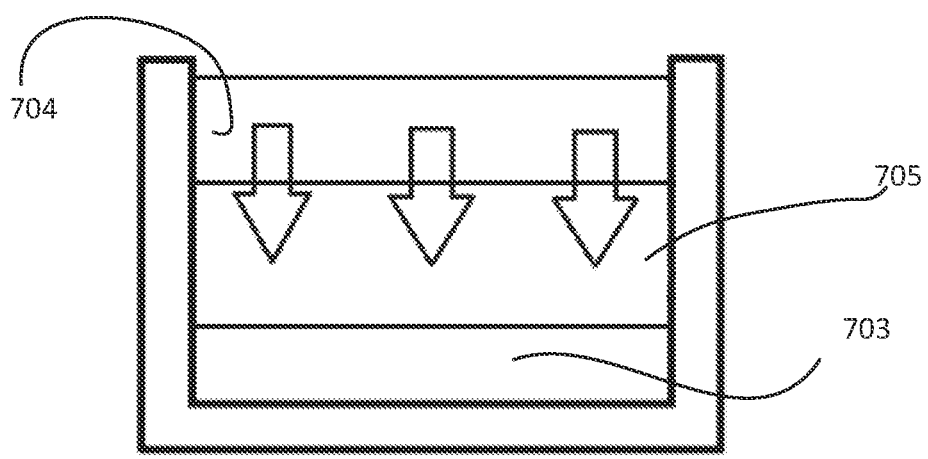
Figure 7C:
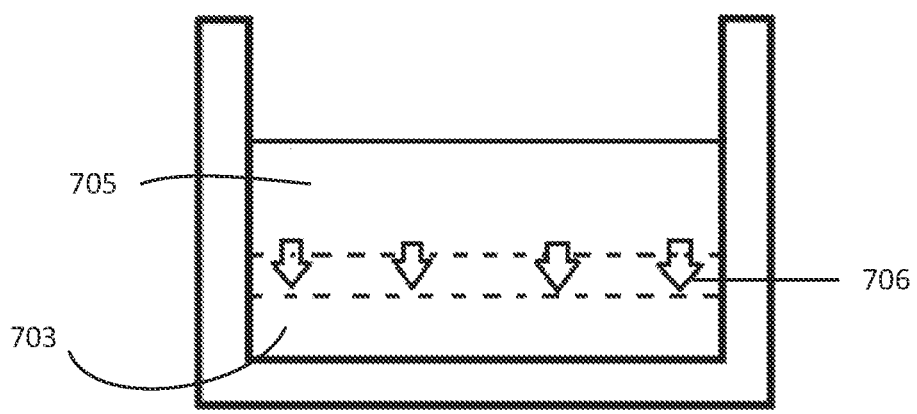

In a further embodiment, illustrated in FIGS. 7a, 7b, and 7c, a sequential, unidirectional infiltration process is provided. In this embodiment, a porous ceramic body (700) is placed within a permeation-resistant casing material (701), wherein a first porous region (703) is positioned above a second porous region (705). In a first step, a volume of diluting liquid (702) in contact with an upward-facing (top) surface (707) of a porous ceramic body (700), is unidirectionally infiltrated (as indicated by the arrows) in a downward direction into the first porous region (703) of the ceramic body (700). After infiltration, the ceramic body is inverted, so that the first porous region (703) is below the second porous region (705). The casing (701) is removed from the upward-facing end surface of the second porous region (705), and downward facing end surface of the first porous region (703) is covered by casing (701).

In a second infiltration step, as illustrated in FIG. 7b, a volume of liquid coloring composition (704) in contact with the porous ceramic body is unidirectionally infiltrated into the second porous region (705). The liquid coloring composition (704) infiltrates downward towards the diluting liquid (702) in the first porous region (703), in the direction of the bottom of the ceramic body. Thus, a sequential, unidirectional infiltration process is provided where in a first step, a diluting liquid is infiltrated into the porous ceramic body in a top-to-bottom direction (y-axis), and upon inverting the porous ceramic body, in a second step, a liquid coloring composition is infiltrated into the porous ceramic body in a top-to-bottom (y-axis) direction.

As illustrated in FIG. 7c, after infiltration of the liquid coloring composition (704) into the second porous region (705), diffusion of the coloring agent and diluting liquid contained within the first porous region (703) form a transition region (706).

In this embodiment, where the side surface of the ceramic body is covered with a permeation resistant casing (701), ingress or egress of the liquid coloring composition (704) and diluting liquid (702) through the side surface of the ceramic body is prevented. Lateral flow (in x-axis and z-axis directions) of the liquid coloring composition within the pore volume of the ceramic body is inhibited by unidirectionally infiltration. While not wishing to be bound by theory, it is believed that in some embodiments, rapid convective mixing of liquid coloring composition and the diluting liquid is inhibited as the flow of the liquid components into and out of the side surfaces and bottom surface of the ceramic body is restricted by a casing material. Where casing material covers the bottom and side surfaces, inhibiting ingress or egress of the liquid coloring composition and diluting liquid into or out of the ceramic body, mixing of the liquid coloring composition and diluting liquid may occur slowly through diffusion within the porous ceramic body.

In an alternate embodiment, a method for infiltrating the porous ceramic body with two liquid coloring compositions is provided. In one embodiment, a first liquid coloring composition is infiltrated into a first porous region, and a second liquid coloring composition is infiltrated into a second porous region that is opposite the first porous region. In this embodiment, a first liquid coloring composition is infiltrated into a first porous region and any excess liquid coloring composition that was not infiltrated is decanted. The porous body may be heated adjacent the first porous region to evaporate liquid component of the first liquid coloring composition and to fix at least a portion of the first liquid coloring composition in the first region. A non-fixed portion of the first liquid coloring composition may infiltrate or diffuse toward the second region to form a smooth color gradient between first and second regions. Subsequently, the ceramic body is, optionally, inverted, and the second liquid coloring composition is infiltrated into the second porous region. Any excess portion of the second liquid coloring composition that has not infiltrated is decanted, and the porous ceramic body is heated adjacent the second porous region to evaporation liquid component of the second liquid coloring composition and fix at least a portion of the second liquid coloring composition. A non-fixed portion of the second liquid coloring composition may infiltrate or diffuse toward the first region to form a second color gradient between first and second regions. In one embodiment, a single transition region is formed between the first and second porous regions that comprises both first and second liquid coloring compositions. In an alternative embodiment, two adjacent transition regions are formed from the two liquid coloring compositions. In one embodiment, the porous ceramic body contains a diluting liquid within a portion of the pore volume, for example, between the first and second color regions. One or both of the first and second coloring compositions may mix with the diluting liquid to form one or more smooth color transition regions.

The diluting liquid may comprise a polar or non-polar, organic or inorganic solvent, such as water or isopropyl alcohol (IPA), or mixtures thereof, and the solvent may be the same or different as the liquid component of the liquid coloring composition (403). Optionally, the diluting liquid may comprise from 0.0001 wt % to 5 wt %, or 0.01 wt % to 5 wt %, of one or more additives. For example, one or more coloring agents may be dispersed, dissolved, or hydrolyzed, as an additive to the diluting liquid. Coloring agents suitable for use as additives include those coloring agents described herein for use in the liquid coloring composition. An additive that imparts antimicrobial properties in the final ceramic body, such as a silver-containing component or molybdenum-containing component, may be added to the diluting liquid. For example, a molybdenum-containing salt such as molybdenum chloride (e.g., $MoCl_3$, $MoCl_4$, or $MoCl_5$), molybdenum-2-ethylhexanoate (Mo [OOCCH $(C_2H_5)C_4H_9]_4$), ammonium heptamolybdate (($NH_4)_6$ $Mo_7O_{24}.4H_2O$), cyclopentadienylmolybdenum(V) tetrachloride ($C_5H_5Cl_4Mo$), or molybdenum(VI) oxide bis(2,4-pentanedionate) ($C_{10}H_{14}MoO_6$) may be suitable for use herein.

In one embodiment, the diluting liquid is infiltrated within porous ceramic body, in an amount between 1 vol % and 100 vol % of the pore volume of the porous ceramic body. In another embodiment, diluting liquid infiltrates between 1 vol % and 99 vol %, or between 3 vol % and 97 vol %, or between 5 vol % and 50 vol %, or between 10% and 85%, or between 10 vol % and 95 vol %, or between 25 vol % and 85 vol %, or between 30 vol % and 80 vol %, or between 40 vol % and 75 vol %, or between 33 vol % and 67 vol %, or between 16 vol % and 45 vol %, of the pore volume of the porous ceramic body.

The porous region containing the diluting liquid may be located anywhere between the upper or lower surfaces of the ceramic body, such as, immediately adjacent the upper or lower surface. In an alternative embodiment, the diluting liquid may be in a porous region that is spaced at a distance from the upper surface, the lower surface, or both the upper and lower surfaces. In one embodiment, a volume of diluting liquid that is at least as great as the pore volume of a region to be infiltrated is provided to the exposed surface of a porous region, and the porous region is uniformly infiltrated throughout the width or thickness of the ceramic body for a given depth of penetration.

In a further embodiment, a ceramic body is fully infiltrated with a diluting liquid, and then, a portion of the diluting liquid is removed to form a dry porous region for infiltration by the coloring composition. In one embodiment, at least 30 wt % of the diluting liquid is removed from the fully filled ceramic body, forming an unfilled or dry porous region for infiltration by the liquid coloring composition, and a region substantially filled with diluting liquid.

The heights (relative to the y-axis) of the one or more color regions and the color gradient region may be controlled by controlling the relative volumes of diluting liquid and liquid coloring composition within the ceramic body. The time allotted for infiltration and mixing also may be selected to control the depth of penetration of colorant in each region and the smoothness of the gradient of the transition region in the final sintered ceramic body.

A method for infiltrating a porous ceramic body to make a polychromatic ceramic body comprises one or more of the following steps: a) infiltrating a porous ceramic body with a diluting liquid; b) removing a portion of the diluting liquid (e.g., by evaporation through heating) to form a first region without a diluting liquid and a second region comprising the diluting liquid; c) unidirectionally infiltrating a liquid coloring composition into the first region of the porous ceramic body; d) contacting the diluting liquid with the liquid coloring composition within the porous structure; e) mixing (e.g., by diffusion) a portion of the liquid coloring composition with a portion of the diluting liquid; and f) forming a color transition region between a first region that contains liquid coloring composition and a second region that contains diluting liquid, wherein the color transition region comprises a gradient mixture of coloring composition and the diluting liquid. Infiltration and mixing may occur at ambient temperature and ambient pressure over a period of time, without modifying or adjusting ambient environmental conditions, such as temperature or pressure. After infiltration in the first and second regions, the ceramic body may be heated to terminate infiltration by drying a portion of the diluting liquid or liquid coloring composition, or to terminate diffusion by fixing coloring agents.

In one method, diluting liquid infiltrates from about 10% to 85% of the pore volume of the ceramic body, forming the first region containing the diluting liquid and a second region, opposite the first region that is devoid of, or unfilled with, diluting liquid. After diluting liquid is infiltrated into the first region, the ceramic body may be inverted, exposing the second surface. Liquid coloring composition may be infiltrated into the second region of the inverted porous ceramic body adjacent a second surface that is opposite the first surface. After infiltrating the second region, liquid coloring composition may further permeate into the ceramic body and mix with the diluting liquid forming a color transition region. Optionally, a portion of the liquid coloring composition may be fixed (e.g., b heating) within the second region and a non-fixed portion may mix with the infiltrated diluting liquid to form a color transition region. By infiltrating only a portion of the ceramic body (i.e., the first region) with diluting liquid, and inverting the ceramic body to expose an unfilled region for infiltration by a coloring composition, a heating step to evaporate a portion of the diluting liquid prior to infiltration by the liquid coloring composition may be eliminated.

The liquid coloring composition comprises a coloring agent and a liquid component. The liquid component may form, for example, a solution, suspension or dispersion with a coloring agent, and the liquid component may comprise a polar or non-polar solvent, an organic or inorganic solvent, such as water or IPA, or mixtures thereof. The liquid coloring composition may be acidic having a pH of less than 7, basic having a pH greater than 7, or neutral with a pH of 7.

Coloring agents may comprise metal-containing components, including metallic compounds and metallic complexes having one or more metallic elements of transition metals from groups 3-14 on the periodic table of elements, rare earth metals, or mixtures of transition metals and rare earth metals. A coloring agent may further comprise a metal-containing components having metals or metal ion(s) including but not limited to Tb, Cr, Er, Co, Mn, Pr, V, Ti, Ni, Cu and Zn, to provide a coloring effect. Metallic oxides, or metallic salts containing anions such as $Cl^-$, $SO_4^{2-}$, $SO_3^{2-}$, $Br^-$, $F^-$, $NO_2^-$, and $NO_3^-$, may be suitable for use herein. Metal-containing components may be soluble in the liquid, or comprise sufficiently small ionic particle size to infiltrate the porous lattice structure of the ceramic body. A coloring agent may comprise a nitrate, chloride, or acetate.

The liquid coloring composition may comprise between 0.1 wt % and 8 wt %, or 0.1 wt % and 15 wt %, metallic coloring agent, calculated as metal ion, based on the total weight of the liquid coloring composition. Alternatively, the coloring composition may comprise between 0.2 wt % and 6 wt %, or 0.2 wt % and 8 wt %, metallic coloring agent, calculated as metal ion, based on the total weight of the coloring composition. Optional additives may be included such as organic pigments that burn off during the pre-sintering or sintering process, may be added to confirm application of the liquid coloring composition to the porous ceramic body.

When applied to porous ceramic bodies, liquid coloring compositions may infiltrate throughout the thickness, or within a portion, of the porosity. The liquid coloring composition may fully or partially infiltrate a porous ceramic body having interconnected porosity, or may fully or partially infiltrate a porous ceramic body having discontinuous porosity. After infiltration, the total amount of metal in the sintered body contributed by the coloring composition measured as metal ions, may comprise between 0.02 wt % and 2 wt %, or between 0.027 wt % and 1.6 wt %, or between 0.03 wt % and 1.4 wt %.

Porous ceramic bodies include green stage bodies, and partially consolidated, or pre-sintered, bisque stage bodies, having densities below full theoretical density of the ceramic sintered form. Ceramic materials include, but are not limited to, alumina, zirconia, and mixtures thereof. Zirconia ceramic bodies may comprise between 85 we/0 and 100 wt % of a zirconia material, or between 90 wt % and 99.7 wt % zirconia material, and, optionally, minor amounts of other materials, such as alumina. Zirconia ceramic material may comprise approximately 85 wt % and approximately 98 wt % zirconia, or stabilized zirconia, based on the total weight of the zirconia ceramic material, or approximately 85 wt % or greater, or approximately 90 wt % or greater, or approximately 95 wt % or greater, zirconia, or stabilized zirconia, based on the total weight of the zirconia ceramic material.

Stabilized zirconia ceramic material includes both fully and partially stabilized zirconia. Stabilized zirconia ceramic powder material suitable for use herein includes, but is not limited to, yttria-stabilized zirconia commercially available from Tosoh USA. Further, zirconia may be stabilized with approximately 0.1 mol % to approximately 8 mol % yttria, or approximately 2 mol % to approximately 6 mol % yttria, or approximately 2 mol % to approximately 6.5 mol % yttria, or approximately 2 mol % to approximately 5.5 mol % yttria, or approximately 2 mol % to approximately 5 mol % yttria, or approximately 2 mol % to approximately 4 mol % yttria.

Ceramic powder may have substantially uniform particle size distribution, for example, an average particle size in a range from approximately 0.005 micron (μm) to approximately 1 μm, or from approximately 0.05 μm to approximately 1 μm. Examples of ceramic material suitable for use herein also include zirconia described in commonly owned U.S. Pat. No. 8,298,329, which is hereby incorporated by reference in its entirety.

Both shaded and unshaded (white) ceramic bodies may be infiltrated with the liquid coloring compositions according to the methods described herein. Pre-shaded ceramic materials include commercially available minable, ceramic blocks that match a specific target shade or a shade range, for example, BruxZir® ceramic blocks (e.g., BruxZir® Shaded 16 series in target shades matching VITA® Classic shades; Glidewell Laboratories, Irvine, Calif.).

Porous ceramic bodies suitable for use herein include blocks having a shape that includes, but is not limited to, a cube, cylinder, disc, near-net, shape, or a porous body in the shape of a final dental restoration. Porous ceramic bodies may be made, for example, by pressing or slip casting ceramic powders, or by automated additive (e.g., 3-D printing) and subtractive (e.g., milling) processes, including CAD and/or CAM processes. Processes include, but are not limited to, those described in commonly owned U.S. Pat. Nos. 9,365,459, 9,434,651, and 9,512,317, all of which are hereby incorporated in their entirety, herein.

Prior to infiltration by a liquid coloring composition, the porous ceramic bodies may be partially densified, for example, by heating or pre-sintering to increase the density to below full theoretical density of the material. Pre-sintering methods may be conducted in accordance with manufacturer instructions. In some embodiments, prior to infiltration pre-sintering proceeds by heating at an oven temperature within the range of 700° C. to 1200° C. for 1 to 2 hours. Porous ceramic bodies include those having a density of 30% to 90%, or 50% to 90%, or 40% to 75%, of full theoretical density of the sintered ceramic body, while maintaining sufficient porosity for partial or complete infiltration of the liquid coloring compositions into the porous ceramic body. In some embodiments, the porous ceramic body may comprise at least 20 vol % porosity, or at least 25 vol % porosity. Alternatively, a porous ceramic body may comprise at least 40 vol %, or at least 60 vol %, or between 20 vol % and 80 vol %, porosity, when measured by Archimedes method.

The porous (e.g., green stage or bisque stage) ceramic body may be infiltrated with the liquid coloring composition before or after shaping into a dental restoration form. The ceramic bodies may be shaped, for example, as a single unit crown, bridge, partial or full denture, based on the individual requirements of a patient.

A method has been found for improving machinability of a color infiltrated ceramic body during a shaping process. In some embodiments, after the infiltration process is complete, and, after the optional heating step to terminate the diffusion of coloring agents, the top surface of the resulting infiltrated body has an increased surface hardness that may result in difficulty of milling or grinding, or result in damage to the milling tool. In one embodiment, the method further comprises a post-infiltration heat treatment step. The color infiltrated porous ceramic body is further heated to a temperature (such as, a bisquing temperature) that is below the sintering temperature of the ceramic material, and optionally, above the degradation temperature of a metallic salt component of the coloring composition. In some embodiments, the color infiltrated ceramic body may be heated at a temperature between 400° C. and 1200° C., or between 800° C. and 1000° C., for a period of time between about 30 minutes and 15 hours. The oven temperature may be raised and/or lowered slowly during the post-colorization heat treatment to prevent cracking due to stress at the interface between the liquid coloring composition infiltrated region and the non-coloring liquid infiltrated region.

The infiltrated ceramic bodies, optionally heated in a post-infiltration heat treatment step, may be milled into the shape of a dental restoration reducing damage to the milling tool. The bisque, milled ceramic bodies are heated in a final sintering step to eliminate residual porosity. Ceramic bodies prepared by the methods disclosed herein may be sintered in accordance with instructions of the manufacturer of commercially available ceramic bodies, or by heating at a temperature, for example, between about 1300° C. and 1600° C., for about 2 hours to 48 hours.

In another embodiment, ceramic material infiltrated with liquid coloring composition may be sintered prior to milling into a dental restoration, to provide single shaded or polychromatic, minable sintered ceramic bodies. Ceramic materials that are infiltrated and sintered prior to milling may have a net shape or size that fits most dental restorations while eliminating excess material for removal. Examples of suitable shaped forms which may be sintered to full theoretical density prior to shaping may be found in commonly owned U.S. Patent Publication No. 2013/0316305, and U.S. Pat. No. D769,449, both of which are hereby incorporated herein in their entirety.

Sintered ceramic bodies made in accordance with unidirectional infiltration methods have a natural polychromatic appearance while maintaining sufficient strength suitable for use in anterior and posterior dental applications, as well as full- and partial-arch dentures and bridges. One or more color regions of the final sintered ceramic bodies may, optionally, correspond to a bleached shade, or a classical shade, for example, corresponding to a Classical A1 to D4 Vita® shade guide.

Test Methods

Flexural Strength Test—3-Point Bend Strength

Flexure tests were performed on sintered materials using the Instron—Flexural Strength following ISO 6872 for preparation of strength testing for dental ceramic. Flexural strength bars were milled and prepared. Once prepared, the bars were placed centrally on the bearers of the test machine so the load applied to a 4 mm wide face was along a line perpendicular to the long axis of the test piece. Then force is applied and the load needed for breaking the test piece (loading rate was 0.5 mm/min) was recorded. The flexural strength is calculated using sample's dimensional parameter and critical load information.

Flexural strength, σ, in MPa was calculated according to the following formula:

$$\sigma = \frac{3Pl}{2Wb^2}$$

where P is the breaking load, in newton; l is the test span (center-to-center distance between support rollers), in millimeters; w is the width of the specimen, i.e. the dimension of the side at right angles to the direction of the applied load, in millimeters; b is the thickness of the specimen, i.e. the dimension of the side parallel to the direction of the applied load, in millimeters. The mean and standard deviation of the strength data was reported. Means should equal or exceed the requirements.

Test bars were prepared by cutting bisque materials taking into consideration the targeted dimensions of the sintered test bars and the enlargement factor (E.F.) of the material, as follows:
starting thickness=3 mm×E.F.;
starting width=4 mm×E.F.; and
starting length=55 mm×E.F.

The cut, bisque bars were sintered and flexural strength data was measured and calculated according to the 3 point flexural strength test described in ISO (International Standard) 6872.

Density

The density strongly depends on the composition and structure of the samples of the ceramic materials. Density calculations for ceramic bodies may be determined by liquid displacement method of Archimedes principle. Distilled water was used as the liquid medium. Density of ceramic samples were calculated using the following formula:

$$\rho = \frac{(W^2 - W^1)}{(W^4 - W^1) - (W^3 - W^2)}$$

ρ=Density (gram/cc);
$W^1$=Weight of empty specific gravity bottle (gram);
$W^2$=Weight of specific gravity bottle with sample (gram);
$W^3$=Weight of specific gravity bottle with sample and distill water (gram);
$W^4$=Weight of specific gravity bottle with distill water (gram).

EXAMPLES

Preparation of Bisque Stage Zirconia Blocks

Porous, bisque-stage, ceramic, zirconia blocks suitable for use in dental restoration applications were formed from yttria-stabilized, zirconia ceramic powder as follows. Bisque stage blocks were prepared using a slip casting method. The yttria-stabilized zirconia powder and a dispersant were added to deionized water to form a slurry having a solids concentration of from about 69 vol % to 80 vol % solids. The slurry was mixed for approximately 5 minutes using a high-shear mixer, then added to the mixing tank of a horizontal bead mill. Horizontal bead milling was performed on the slurry at a rate of from about 6 to about 16 kg dry mass per hour to obtain a slip for slip casting. After milling, the slurry was drained from the mixing tank of the horizontal bead mill and passed through a 20 μm sieve to remove milling media.

The slip obtained from the horizontal bead mill was cast into molds to form cast blocks. A mold was used to form disk shaped blocks having a size of 98 mm diameter×15 mm thickness. After casting, the blocks were placed in a dryer at ambient temperature and weighed at 12 hour increments until the weight of the block had stabilized to form green body blocks. Dry green body blocks were loaded into an oven where the blocks were bisque fired at a final hold temperature of 950° C. for a hold time of two hours to form bisque stage ceramic blocks.

Example 1

A polychromatic zirconia ceramic body having two color regions separated by a smooth color transition region was prepared by unidirectional infiltration of liquid coloring composition into a porous zirconia ceramic body prior to sintering.

A liquid coloring composition was prepared by dissolving 17.54 g of metallic salts (wherein the metallic salts comprised the metals of Tb, Cr, Er, and Co) in 150 ml of a 35 vol % deionized (DI) water to 65 vol % IPA solution.

A bisquestage, porous, yttria-stabilized zirconia ceramic block, prepared by the slip-casting process as described above and heated in a bisquing stage, was soaked in water as a diluting liquid for about 90 minutes to completely infiltrate the porous ceramic body with about 45.5 g water. The bisque-stage ceramic block was partially dried by heating on the top surface to eliminate water from the upper region of the porous ceramic block to provide space for infiltration by the liquid coloring composition, while maintaining a portion of the water in a lower region.

The bisqued ceramic block was placed in a polyurethane casing that conformed to side and bottom ceramic block surfaces, leaving only the top surface exposed. The casing was comprised of a material which was resistant to penetration of the coloring composition for the duration of the infiltration process. The polyurethane casing with the bisque ceramic block was placed in a plastic container of an infiltration set-up made substantially according to FIG. 3.

The liquid coloring composition was introduced into the plastic container which formed a reservoir for the liquid coloring composition on the exposed top surface of the porous bisqued ceramic block. The liquid coloring composition was allowed to contact and infiltrate the top surface of the porous ceramic between three and five hours at ambient temperature and pressure. A portion of the coloring composition infiltrated the upper region of the ceramic block was mixed with, and diluted with, remaining water within the porous structure. Excess coloring composition was removed from the infiltration set-up, and the infiltrated ceramic block was held for an additional period of between two and five hours at bench-top. The infiltrated block was removed from the infiltration set-up and polyurethane casing. Infiltration was unidirectional, from the top surface into the upper region and toward the bottom surface of the porous bisque ceramic block. No coloring composition permeated through the casing to enter or exit the side surface of the porous ceramic block, and no coloring composition permeated into or out of the bottom surface of the porous ceramic block.

The color-infiltrated, bisque-stage porous ceramic block was dried to remove the liquid component of the coloring composition and diluting liquid, and then heated at an oven temperature between 700° C. and 1000° C. for 1 hour.

The dried, bisque ceramic block was milled into the shape of a dental crown, wherein the incisal part was milled from the lower region proximate the bottom surface of the block, and the cervical region of the crown was milled from the upper region proximate the top surface of the block; the milled shape was sintered to full density between 1450° C. and 1550° C. for about 2 hours.

The resulting polychromatic sintered dental crown comprised two color regions and a smooth color transition region between the first and second color regions. Upper region of the sintered crown comprised about 50 percent of the crown height, the transition region comprised about 30 percent of the crown height, and the lower region comprised about 20 percent of the crown height. The transition region had a smooth color gradient without sharp boundaries between the two color regions.

Example 2

A polychromatic sintered ceramic block was prepared from a ceramic powder comprising yttria stabilized zirconia material that was pressed and heated to form a porous, bisque-stage ceramic block.

The coloring solution was prepared by dissolving 9.4 g of metallic salt (wherein the metallic salts comprised the metals of Tb, Cr, Er, and Co) into 50 ml of IPA.

The dry, porous, bisque-stage, ceramic block was placed in a polyurethane casing that conformed to side and bottom surfaces, and then placed within an infiltration set-up substantially according to Example 1. No diluting liquid was added to the bisque-stage, ceramic block prior to infiltration with the coloring solution. Infiltration was at ambient temperature with coloring solution for 1 hour and 30 minutes without the addition of pressure. After infiltration, the excess coloring solution was removed from the infiltration set-up. The infiltrated block was removed from the infiltration set-up and casing, dried for 30 minutes at 85° C. and then sintered at 1550° C. for 6 hours.

The sintered polychromatic block showed uniform color infiltration forming a first color region adjacent a second color region that corresponded to the original block color. There was no color gradient region between the infiltration color and block color regions that was detectable with the unaided eye, thus, the polychromatic block lacked a smooth color transition zone between the two color regions.

Example 3

A polychromatic ceramic body was prepared by unidirectional infiltration of liquid coloring composition into a bisque-stage, porous, zirconia ceramic block prior to sintering.

An yttria-stabilized, bisque-stage, ceramic zirconia body was prepared by a slip-casting technique as described above. The bisque-stage, ceramic zirconia body was inserted in a polyurethane casing and an infiltration set-up substantially according to Example 1.

A liquid coloring composition formed substantially in accordance with Example 1, was allowed to infiltrate the bisque-stage, ceramic zirconia body between three and five hours at ambient temperature and pressure. The liquid coloring composition infiltrated to fill a porous region extending for only a portion of the height of the block. No diluting liquid was infiltrated into the block prior to infiltration by the liquid coloring composition. Excess liquid coloring composition was removed from the infiltration set-up, and the infiltrated ceramic block was held for an additional period between two and five hours at bench-top. After holding at bench top, the infiltrated ceramic block was subsequently heated. The top surface of the infiltrated ceramic block was heated to dry and to fix coloring agents of the coloring composition that infiltrated near the top surface. Part of the metallic salt component which was not fixed in position by the heating step continued to infiltrate through a portion of the infiltrated ceramic block. The color-infiltrated ceramic block was then heated at an oven temperature between 700° C. and 1000° C. for about one hour.

A dental crown was milled from the heat-treated infiltrated, ceramic block, wherein the cervical area was milled from the region near the top surface and the incisal/occlusal edge was milled from a region near the bottom surface of the ceramic block. The dental crown was sintered between 1450° C. and 1550° C. for about two hours. The sintered dental crown had a darker color region in the tooth body area and tooth cervical area of the crown, a lighter color region near the incisal/occlusal edge, and a color transition region between the darker and lighter color regions. The color transition region was gradual and smooth, having no sharp color boundaries appearing between the color regions.

Examples 4 and 5

Coloring solution was unidirectionally infiltrated into green and bisque-stage, porous, zirconia, ceramic blocks to form polychromatic ceramic bodies.

Yttria-stabilized zirconia, porous, green and bisque stage, disc blocks were prepared substantially according to the slip-casting method described above. The porous, green and bisque blocks were placed in polyurethane casings that covered the side and bottom surfaces, and then the blocks were placed in an infiltration set-up substantially according to Example 1.

A coloring solution was prepared by dissolving 9.4 g of metallic salt (wherein the metallic salts comprised the metals of Tb, Cr, Er, and Co) into 50 ml of IPA.

Half of the green bodies and half of the bisque-stage porous ceramic blocks were infiltrated by the coloring solution at ambient temperature and without the addition of pressure for 15 hours. Half of the green blocks and half of the bisque-stage porous ceramic blocks were infiltrated by the coloring solution at ambient temperature under 40 psi pressure for 15 hours. Pressure infiltration at 40 psi was conducted after putting the whole infiltration setup into a pressure chamber (Bego Wiropress SL Pressure Vessel). For all infiltration processes, no water or other diluting liquid was infiltrated into the blocks prior to infiltration by the coloring solution. After infiltration by the coloring solution, all blocks were dried in the oven at 90° C. for 30 min. After drying, the infiltrated blocks were sintered between 1450° C. and 1550° C. for two hours.

All sintered, infiltrated blocks showed uniform color infiltration throughout the ceramic mass, forming an upper color region, and an adjacent lower color region that corresponded to the original block color. The infiltrated blocks did not show smooth color transition zones between the upper and lower color regions. No noticeable infiltration difference between "no pressure" and "40 psi" for both "green sample" and "bisque sample" was observed. Coloring solution infiltrated much deeper into "bisque sample" than into "green sample".

Example 6

A polychromatic ceramic body was prepared by unidirectional infiltration of a coloring solution into a bisque stage, porous zirconia ceramic body prior to sintering.

An yttria-stabilized zirconia bisque block having thickness of 15 mm was prepared substantially according to the slip-casting method described above. The porous bisque block was placed in polyurethane casing that covered and conformed to the side and bottom surface, and then, the ceramic block was placed in an infiltration set-up substantially according to Example 1.

A coloring solution was prepared by dissolving 6.26 grams of metallic salt (wherein the metallic salts comprised the metals of Tb, Cr, Er, and Co)] into 50 ml of IPA.

The bisqued block was infiltrated with the coloring solution between three and five hours without prior infiltration with water or other diluting liquid. Excess coloring solution was decanted from the top of the block. The block was held at ambient temperature on the bench between two and five hours, and then dried in the oven at 90° C.

The dried block was removed from the infiltration set-up and casing, and then bisqued between 700° C. and 1000° C. for one hour. Twenty-one identical teeth were milled from different locations at the same vertical distance relative to the top surface of the block, and were sintered between 1450° C. and 1550° C. for 2 hour.

Colorization was uniform among all 21 teeth, with all 21 teeth having uniform, identical color regions, and identical smooth color transition regions, demonstrating uniform infiltration of the coloring solution into the thickness of the whole block, throughout the color regions and transition region.

Examples 7-9

A polychromatic ceramic body was prepared by unidirectional infiltration of a coloring solution into a bisqued, porous, zirconia ceramic body prior to sintering.

An yttria-stabilized, zirconia, bisque block having thickness of 15 mm was prepared substantially according to the slip-casting method described above. The porous, bisque, block was placed in polyurethane casing that covered and conformed to the side and bottom surfaces, and then was placed in an infiltration set-up substantially according to Example 1.

A coloring solution was prepared by dissolving 6.26 grams of metallic salt (wherein the metallic salts comprised the metals of Tb, Cr, Er, and Co) into 50 ml of IPA.

Deionized (DI) water, as a diluting liquid, was infiltrated into porous, bisque, block for 1 hr. 30 min. followed by drying between two and five hours to remove a portion of the infiltrated diluting liquid. The dried block was infiltrated with coloring solution between three and five hours. Excess coloring solution was decanted, and then, the block was held on the bench between two and five hours at ambient temperature. The block was dried at 90° C. for 30 minutes, and then was bisqued between 700° C. and 1000° C. for an hour. After the bisquing, two different sets of samples were milled from two different locations of the infiltrated blocks. The first set of samples was milled from the main body color zone, and the second set of samples was milled from the transition zone. The third set of samples was milled from the white, non-infiltrated yttria-stabilized zirconia zone. All three sets of samples were sintered between 1450° C. and 1550° C. for two hours, and then mechanically tested for 3-point bend strengths.

Eight to ten bend bars were prepared from each of the three sets of testing samples. The 3-point bend strengths of the non-infiltrated samples, transition-colored samples, and main body-colored samples were 825±136 MPa, 868±46 MPa, 800±96 MPa, respectively, indicate that mechanical strength was not affected by infiltration of different levels of coloring solution.

Examples 10-13

Polychromatic zirconia ceramic bodies were prepared by unidirectional infiltration of liquid coloring compositions into a porous zirconia ceramic body.

Liquid coloring compositions were prepared by dissolving approximately 30 g to 40 g of metallic salts (wherein the metallic salts comprised the metals of Pr, Cr, Er, and Co) in approximately 150 ml to 250 ml deionized (DI) water. Diluting liquids were selected from either deionized water having no coloring component, or a solution comprising approximately 18.4 g of the above-listed metallic salts, as a colorant, dissolved in 150 ml to 250 ml of deionized water.

Porous yttria-stabilized zirconia ceramic blocks were prepared. The disc-shaped blocks two having the dimension of 18 mm thickness and 98 mm diameter, and two having a thickness of 31.5 mm and 98 mm diameter, had porosities in the range of 50 vol % to 65 vol % after heating in a bisquing stage. Side surfaces were covered with casing material during infiltration processes. The end surface of each block was not covered when in an upwardly facing position for infiltration, leaving it exposed for infiltration of diluting liquid or coloring compositions through this surface. The end surface of each block were covered in casing material when in a downwardly facing position during infiltration to prevent the infiltrating liquids from penetrating through the bottom of the ceramic block.

Examples 10 and 11

Two of the ceramic disc-shaped blocks described above (18 mm thickness and 98 mm diameter) were infiltrated through exposed upwardly facing surfaces. One block (Ex. 10) was infiltrated with 100 ml-250 ml deionized water for 2 minutes to 5 minutes; the second block (Ex. 11) was infiltrated with diluting liquid with colorant for 2 minutes to 5 minutes. The blocks were inverted, and infiltrated with a coloring solution for 10 minutes to 90 minutes. After infiltration with coloring liquid, the blocks were held at the bench for 20 minutes to 120 minutes at ambient temperature, then dried at 120° C. for 30 minutes before heating to a bisquing temperature between 700° C. and 1000° C. for two hours. After bisquing, one three-unit bridge and one single tooth were milled from each block, and sintered between 1450° C. and 1550° C. for two hours.

The sintered teeth of the three-unit bridges and each individual tooth had a darker shaded upper body region and a lighter shaded incisal region with a smooth color transition region there between. The shade of the color transition region decreased in intensity between the body shade and the incisal shade regions, with no sharp distinguishable transition lines between the regions. For the restorations milled from the ceramic block in which water was used as the diluting liquid (Ex. 10), the shade of the incisal regions matched the shade of the sintered, original block material; for the restorations milled from the ceramic block infiltrated with a diluting liquid having a colorant (Ex. 11), the shade of the cervical and body regions were darker than the sintered, original unshaded ceramic block.

Examples 12 and 13

Two ceramic blocks described above (disc-shaped, 31.8 mm thickness and 98 mm diameter) were infiltrated through exposed upwardly facing surfaces with the diluting liquid having a metal colorant. One ceramic block (Ex. 12) was infiltrated with diluting liquid for 1 minutes to 3 minutes; the second ceramic block (Ex. 13) was infiltrated with the diluting liquid for 9 minutes to 15 minutes. After infiltration by diluting liquid, the blocks were inverted and the opposite end surfaces were infiltrated with a liquid coloring solution. The block of Ex. 12, was infiltrated with coloring solution for 10 minutes to 30 minutes; the block of Ex. 13 was infiltrated with coloring solution for 30 minutes to 120 minutes. After infiltration with liquid coloring solution, the blocks were held at the bench for 20 minutes to 120 minutes at ambient temperature, then dried at 120° C. for 30 minutes, before bisquing between 700° C. and 1000° C. for one hour. After bisquing, the blocks were sintered between 1450° C. and 1550° C. for two hours.

For the infiltrated ceramic block of Ex. 12, a cross-sectional view after sintering revealed three distinct regions: a dark color region adjacent one end surface, a lighter color region adjacent the opposite end surface, and a middle region. The middle region had a color consistent with the unshaded ceramic block indicating the coloring solution and/or diluting liquid did not penetrate this region. Sharp transition lines appeared between the dark color region and the middle region, and there was no color gradient region between the two color regions. The sharp transition lines and lack of color gradient indicated an insufficient amount of infiltration to enable dilution of the coloring agent of the liquid coloring solution by the diluting liquid to occur.

For the block according to Ex. 13, a cross-sectional view of the sintered body showed a dark color region adjacent one end surface, a lighter color region adjacent the opposite end surface, and a smooth transition region in between the two color regions. The transition region's color decreased in intensity from the dark color region to the lighter color region. No sharp or noticeable transition lines occurred between the color regions and the transition region, indicating that the infiltrated liquid coloring solution came in contact with the infiltrated diluting liquid, and the coloring agent of the liquid coloring solution was diluted by the diluting liquid to form the color transition region.

We claim:

1. A method of coloring a ceramic body for use in dental applications comprising:
   a. obtaining a porous ceramic body comprising
      i. a first end surface adjacent a first porous region,
      ii. a second end surface adjacent a second porous region, opposite the first end surface, and
      iii. a side surface that extends between the first end and second end surfaces;
   b. infiltrating a diluting liquid through the first end surface to occupy a first porous region adjacent the first end;
   c. preventing the diluting liquid from passing through the second end surface and the side surface;
   d. infiltrating a liquid coloring composition comprising a liquid component and a coloring agent through the second end surface to occupy the second porous region adjacent the second end surface,
   e. preventing the liquid coloring composition and the diluting liquid from passing through the first end surface and side surface;
   f. contacting a portion of the liquid coloring composition in the second porous region with a portion of the diluting liquid in the first porous region; and
   g. forming a color gradient region, wherein the coloring agent has a concentration that decreases from the second porous region towards the first porous region.

2. The method of claim 1, wherein the liquid coloring composition contacts the diluting liquid at an interface and the coloring agent is diluted by the diluting liquid adjacent the interface.

3. The method of claim 1, wherein during infiltrating the diluting liquid, the first porous region is positioned above the second porous region, and the diluting liquid is infiltrated into the ceramic body through the first end surface downwardly into the first porous region.

4. The method of claim 3, further comprising inverting the porous ceramic body after infiltrating the diluting liquid to position the second porous region above the first porous region, and the liquid coloring composition is infiltrated from the second end surface downwardly into the second porous region.

5. The method of claim 1, comprising unidirectionally infiltrating the diluting liquid from the first end surface into the first porous region, and unidirectionally infiltrating the liquid coloring composition from the second end surface into the second porous region, wherein the diluting liquid and the liquid coloring composition are infiltrated sequentially.

6. The method of claim 1, comprising infiltration between 3% by volume and 75% by volume porosity of the porous ceramic body with the diluting liquid, and infiltrating between 25% by volume and 97% by volume porosity of the porous ceramic body with the liquid coloring composition.

7. The method of claim 1, further comprising heating the porous ceramic body to fix a first portion of the coloring agent in a position within the porous ceramic body, and for a second portion of the coloring agent that is not fixed, diffusing the second portion within the porous ceramic body.

8. The method of claim 1, wherein the diluting liquid comprises a solvent selected from a polar or non-polar solvent.

9. The method of claim 1, wherein the liquid coloring composition comprises at least one metallic salt as a first coloring agent.

10. The method of claim 9, wherein the diluting liquid comprises a second coloring agent.

11. The method of claim 10, wherein the second coloring agent of the diluting liquid has a metallic salt concentration that is less than a metallic salt concentration of the first coloring agent in the liquid coloring composition.

12. The method of claim 1, wherein the porous ceramic body is a zirconia ceramic body.

13. The method of claim 1, comprising fully infiltrating the porous ceramic body with the diluting liquid and removing a first volume of the diluting liquid from the porous ceramic body, wherein a second volume of the diluting liquid occupies the first porous region.

14. A method of coloring a ceramic body for use in dental applications, comprising:
   a. positioning a porous ceramic body within an enclosure of an infiltration apparatus, wherein the porous ceramic body comprises a side surface, a first end surface adjacent a first porous region, and a second end surface adjacent a second porous region opposite the first end surface;
   b. providing a volume of a diluting liquid within the enclosure on the first end surface of the porous ceramic body;

c. infiltrating the diluting liquid through the first end surface of the ceramic body into a first porous region of the porous ceramic body;
d. preventing the diluting liquid from passing through the second end surface and the side surface of the porous ceramic body;
e. inverting the porous ceramic body within the enclosure;
f. providing a volume of a liquid coloring composition comprising a liquid component and a coloring agent within the enclosure on the second end surface;
g. infiltrating the liquid coloring composition through the second end surface into a second porous region that is adjacent the first porous region;
h. preventing the diluting liquid and liquid coloring composition from passing through the first end surface and the side surface of the porous ceramic body;
i. contacting a portion of the liquid coloring composition in the second porous region with a portion of the diluting liquid in the first porous region, and then mixing to form a color gradient region having a concentration of coloring agent that decreases from the second porous region to the first porous region;
j. optionally, drying the infiltrated ceramic body, and bisquing, the infiltrated porous ceramic body;
k. optionally, shaping the infiltrated porous ceramic body; and
l. sintering to form a sintered ceramic body comprising a first color region adjacent a first end surface, a second color region adjacent the second end surface, and a color gradient region there between.

15. The method of claim 14, comprising unidirectionally infiltrating the diluting liquid from the first end surface into the first porous region, and unidirectionally infiltrating the liquid coloring composition from the second end surface into the second porous region, wherein the diluting liquid and the liquid coloring composition are infiltrated sequentially.

16. The method of claim 14, wherein when the porous ceramic body is positioned in the infiltration apparatus, the first porous region is above the second porous region and the diluting liquid is infiltrated from the first end surface downwardly into the first porous region, and upon inverting the porous ceramic body, the second porous region is above the first porous region and the liquid coloring composition is infiltrated from the second end surface downwardly into the second porous region.

17. The method of claim 14, wherein a total volume of liquid coloring composition and diluting liquid provided to the enclosure is greater than a total pore volume of the porous ceramic body.

18. The method of claim 14, wherein the color gradient region comprises a smooth color transition between the first and second color regions upon sintering the porous ceramic body.

19. A method of coloring a ceramic body for use in dental applications comprising:
   a. obtaining a porous ceramic block for use in machining a dental restoration comprising
      i. a first end surface adjacent a first porous region,
      ii. a second end surface adjacent a second porous region, opposite the first end surface, and
      iii. a side surface that extends between the first and second end surfaces;
   b. providing a volume of a liquid coloring composition comprising a liquid component and a coloring agent directly above the second end surface,
   c. infiltrating the liquid coloring composition downwardly into the second porous region;
   d. fixing a first portion of the liquid coloring composition in the second porous region by heating; and
   e. diffusing a second portion of the liquid coloring composition that was not fixed in the heating step into the first porous region forming a color gradient region in the first porous region.

\* \* \* \* \*